United States Patent
George et al.

(10) Patent No.: US 10,905,623 B2
(45) Date of Patent: Feb. 2, 2021

(54) MULTI-ACTION LIP-ENHANCEMENT DEVICE

(71) Applicant: L'OREAL, Paris (FR)

(72) Inventors: Kelly George, Denville, NJ (US); Zane Miller, Seattle, WA (US); Janet Wangari-Talbot, Hillsborough, NJ (US); Destenee Green, Jersey City, NJ (US)

(73) Assignee: L'OREAL, Paris (FR)

( * ) Notice: Subject to any disclaimer, the term of this patent is extended or adjusted under 35 U.S.C. 154(b) by 438 days.

(21) Appl. No.: 15/663,150

(22) Filed: Jul. 28, 2017

(65) Prior Publication Data

US 2019/0029917 A1    Jan. 31, 2019

(51) Int. Cl.
*A61H 9/00* (2006.01)
*A61H 23/00* (2006.01)
(Continued)

(52) U.S. Cl.
CPC ............ *A61H 9/0057* (2013.01); *A45D 44/22* (2013.01); *A61B 5/0537* (2013.01); *A61B 5/682* (2013.01);
(Continued)

(58) Field of Classification Search
CPC ........ A61M 1/08; A61M 1/00; A61M 1/0066; A61M 1/0068; A61M 2230/005; A61M 2205/07; A61M 2209/06; A61M 2210/0637; A61M 2210/0625; A61M 1/0072; A61M 2205/054; A61M 2205/055; A61M 2205/106; A61M 2205/3303; A61M 2205/3317; A61M 2205/3334; A61M 2205/3344; A61M 2205/35;
(Continued)

(56) References Cited

U.S. PATENT DOCUMENTS 5,116,206 A * 5/1992 Adahan ................. F04B 53/143
    417/234
7,287,923 B1 * 10/2007 Chen ....................... A45D 40/24
    132/317
(Continued)

FOREIGN PATENT DOCUMENTS

CN    204932599 U * 1/2016
DE    20 2007 001 473 U1    5/2007
(Continued)

OTHER PUBLICATIONS

International Search Repot and Written Opinion dated Oct. 11, 2018 in PCT/US2018/044043, 14 pages.

*Primary Examiner* — Rachel T Sippel
*Assistant Examiner* — Benjamin M. Kusiak
(74) *Attorney, Agent, or Firm* — Oblon, McClelland, Maier & Neustadt, L.L.P.

(57) ABSTRACT

A lip conditioning device for providing enhanced tissue therapy to lip tissue of a user, the device including a mouthpiece having a chamber with a distal end configured to create a seal with a portion of lip tissue of a user; a base portion, connected to the mouthpiece, including a controller in communication with a power source, and a suction device configured to remove air within the chamber; and a set of controls, in communication with the controller, configured to control a mode of operation of the tissue therapy.

15 Claims, 23 Drawing Sheets

(51) Int. Cl.
*A61M 1/00* (2006.01)
*A61N 1/32* (2006.01)
*A61B 5/00* (2006.01)
*A61N 1/18* (2006.01)
*A61B 5/053* (2006.01)
*A61N 1/04* (2006.01)
*A45D 44/22* (2006.01)
*A61H 7/00* (2006.01)
*A61M 1/08* (2006.01)

(52) U.S. Cl.
CPC ......... *A61H 7/008* (2013.01); *A61H 9/0007* (2013.01); *A61H 23/00* (2013.01); *A61M 1/0025* (2014.02); *A61M 1/0031* (2013.01); *A61M 1/0037* (2013.01); *A61M 1/0088* (2013.01); *A61N 1/0452* (2013.01); *A61N 1/18* (2013.01); *A61N 1/328* (2013.01); *A61H 2201/165* (2013.01); *A61H 2205/022* (2013.01); *A61M 1/0068* (2014.02); *A61M 1/0072* (2014.02); *A61M 1/08* (2013.01); *A61M 2205/05* (2013.01); *A61M 2205/054* (2013.01); *A61M 2205/3553* (2013.01); *A61M 2205/364* (2013.01); *A61M 2205/52* (2013.01); *A61M 2210/0625* (2013.01); *A61M 2230/005* (2013.01); *A61M 2230/63* (2013.01); *A61M 2230/65* (2013.01)

(58) Field of Classification Search
CPC .. A61M 2205/3546; A61M 2205/3553; A61M 2205/3561; A61M 2205/3673; A61M 2209/01; A61M 2210/0606; A61M 2230/65; A61H 9/0057; A61H 9/2201; A61H 9/0153; A61H 9/0176; A61H 9/018; A61H 9/105; A61H 9/169; A61H 9/5005; A61H 9/0107; A61H 9/0157; A61H 9/0196; A61H 9/1645; A61H 9/1604; A61H 9/2205; A61H 9/02; A61H 9/022; A61H 9/026; A61H 7/00; A61H 7/001; A61H 7/007; A61H 7/008; A61H 9/005; A61H 2201/0207; A61H 2201/228; A61H 2201/501; A61H 2201/5071; A61H 2205/022; A45D 33/26; A45D 40/00; A45D 40/18; A45D 40/24; A45D 2040/0018; A45D 2040/0043; A45D 2040/005; A45D 2040/0056; A45D 2040/0025; A45D 44/22

USPC ........ 601/1, 6–8, 10–12; 132/294, 297, 317, 132/318, 320

See application file for complete search history.

(56) References Cited

U.S. PATENT DOCUMENTS

| | | | |
|---|---|---|---|
| 10,376,737 | B1 * | 8/2019 | Shepherd ............... A63B 23/03 |
| 2003/0062060 | A1 * | 4/2003 | Burroughs ........... A45C 11/008 |
| | | | 132/297 |
| 2007/0016277 | A1 | 1/2007 | Karat et al. |
| 2013/0046211 | A1 * | 2/2013 | Ho ......................... A61M 1/08 |
| | | | 601/6 |
| 2013/0110014 | A1 | 5/2013 | Luzon et al. |
| 2013/0158447 | A1 | 6/2013 | Shabazian |
| 2014/0081183 | A1 | 3/2014 | Gomez |
| 2014/0135175 | A1 | 5/2014 | Shepherd et al. |
| 2016/0045389 | A1 * | 2/2016 | Goonetilleke ....... A61H 9/0057 |
| | | | 601/11 |
| 2016/0242989 | A1 | 8/2016 | Alexander et al. |
| 2017/0056636 | A1 | 3/2017 | Shadduck |
| 2017/0290732 | A1 * | 10/2017 | Palomaki ................. A61H 9/00 |
| 2018/0185235 | A1 | 7/2018 | Nelson et al. |
| 2018/0318165 | A1 * | 11/2018 | Donda .................... A61F 13/00 |
| 2018/0344534 | A1 * | 12/2018 | Daich ................. A61M 1/0088 |
| 2019/0151156 | A1 * | 5/2019 | Kieswetter ....... A61F 13/00068 |

FOREIGN PATENT DOCUMENTS

| | | | | |
|---|---|---|---|---|
| EP | | 0365230 A2 * | 4/1990 | ............ A61H 9/005 |
| WO | WO 2017/007939 A1 | | 1/2017 | |
| WO | WO 2017/177020 A1 | | 10/2017 | |

* cited by examiner

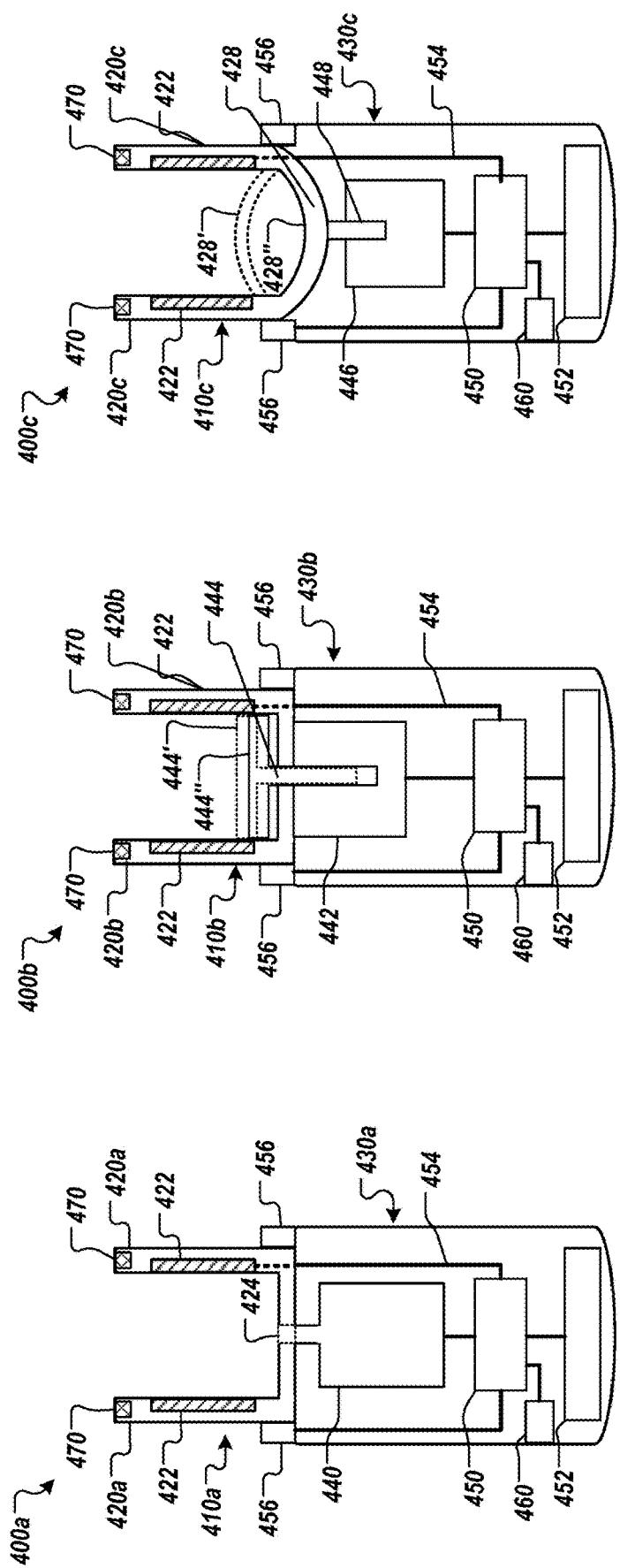

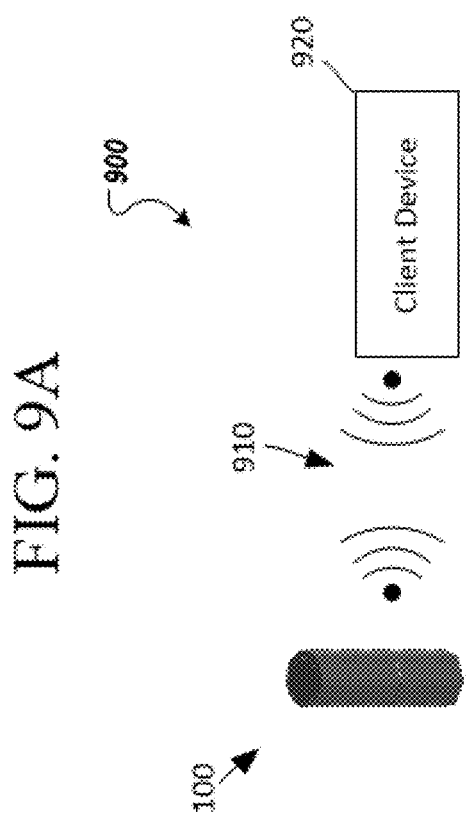

MULTI-ACTION LIP-ENHANCEMENT DEVICE

BACKGROUND

The present disclosure describes a personal care appliance for use in beauty and care of lip tissue.

SUMMARY

In an embodiment, a lip conditioning device is provided for providing enhanced tissue therapy to lip tissue of a user, the device comprising: a mouthpiece having a chamber with a distal end configured create a seal with a portion of lip tissue of a user; a base portion, connected to the mouthpiece, including a controller in communication with a power source, and a suction device configured to remove air within the chamber; and a set of controls, in communication with the controller, configured to control a mode of operation of the tissue therapy.

In an embodiment, the suction device includes a vacuum and a regulator configured to oscillate the vacuum at a predetermined frequency, where the regulator changes the vacuum from a negative pressure value to atmospheric pressure and then back to the negative pressure value over one period.

In an embodiment, the regulator is configured to oscillate the vacuum between two or more negative pressure values at a predetermined frequency.

In an embodiment, the suction device includes a piston and a motor assembly configured to move the piston, and the piston is configured to move within the chamber while maintaining a seal with an inner surface of the chamber.

In an embodiment, the mouthpiece has a flexible diaphragm forming a portion of the chamber, wherein the base portion has a plunger connected to a motor assembly configured to move the flexible diaphragm within the chamber.

In an embodiment, there is provided a pressure sensor configured to detect a suction pressure.

In an embodiment, there is provided a physiologic sensor configured to detect at least one of a change in blood flow and a tissue property.

In an embodiment, there is provided a heater configured to provide heat to the lip tissue of the user.

In an embodiment, there is provided an applicator configured to deliver a lip serum to the lip tissue of the user, wherein the heater is configured to perform catalytic heating to enhance seeping of active ingredients of the lip serum within layers of the lip tissue of the user.

In an embodiment, there is provided one or more electrodes configured to sense a lip tissue condition of a portion of the lip tissue of the user.

In an embodiment, the lip tissue condition is at least one of an amount of hydration and/or moisture, an amount of cracking, and a thickness related to the lips of the user.

In an embodiment, the lip conditioning device is configured to provide a tissue therapy to the lip tissue of the user based on a tissue therapy regimen that is determined based on the sensed lip tissue condition of the user.

In an embodiment, the lip conditioning device is configured to communicate the sensed lip tissue condition to an external device, and the external device determines and transmits control information for administering the tissue therapy regimen to the lip conditioning device based on the sensed lip tissue condition.

In an embodiment, the controller is configured to control a visual indicator to provide an indication of a status of at least one of the sensed lip tissue condition and a progress of the tissue therapy regimen.

In an embodiment, the one or more electrodes are disposed surrounding an opening of the chamber.

In an embodiment, the one or more electrodes are configured to provide electromyostimulation to the lip tissue of the user.

In an embodiment, there is provided a vibrator configured to provide a vibration to the lip tissue of the user at a predetermined frequency.

In an embodiment, a method is provided, implemented by a lip conditioning device for providing enhanced tissue therapy to lip tissue of a user, comprising: sensing a lip tissue condition of a portion of lip tissue; determining a tissue therapy regimen based on the lip tissue condition; and automatically providing a tissue therapy to the portion of lip tissue based on the tissue therapy regimen.

In an embodiment, the tissue therapy includes at least one of: creating a suction to a portion of the lip tissue; providing heat to the portion of lip tissue; providing electromyostimulation of the portion of lip tissue; and providing a vibration to the portion of lip tissue.

In an embodiment, a system is provided comprising: a lip conditioning device for providing enhanced tissue therapy to lip tissue of a user, the lip conditioning device including a mouthpiece having a chamber with a distal end configured create a seal with a portion of lip tissue of a user, a base portion, connected to the mouthpiece, including a controller in communication with a power source, and a suction device configured to remove air within the chamber, and a set of controls, in communication with the controller, configured to control a mode of operation of the tissue therapy; and an information processing device configured to communicate with the lip conditioning device and provide control information for controlling the mode of operation.

BRIEF DESCRIPTION OF THE DRAWINGS

A more complete appreciation of the disclosed embodiments and many of the attendant advantages thereof will be readily obtained as the same becomes better understood by reference to the following detailed description when considered in connection with the accompanying drawings, wherein:

FIG. 4A is a drawing of a cross section of a lip device including a mouthpiece having a chamber having a port and a base portion having a vacuum connected to the chamber through the port according to an example;

FIG. 4B is a drawing of a cross section of a lip device including a mouthpiece having a chamber and a base portion having a plunger configured to move within the chamber while maintaining a seal with an inner surface of the chamber according to an example;

FIG. 4C is a drawing of a cross section of a lip device including a mouthpiece having a flexible diaphragm forming a portion of a chamber, and a base portion having a plunger configured to move the flexible diaphragm within the chamber according to an example;

FIG. 9A shows a system that includes a lip device, as discussed above, and a client device, according to an embodiment;

DETAILED DESCRIPTION

A lip device is provided for performing enhanced tissue therapy to lip tissue of a user. Examples of lip therapies include multimodality stimulation, microsuction, electromyostimulation, and catalytic heating. The lip device can be used by a user to increase their lip volume, give an appearance of plumper lips, and to modify a lip color. Use of the lip device is configured to improve an overall condition of the lip tissue including increased moisture retention resulting in soft and smooth lips, as well as visible reduction in aging of the lip tissue such as reduction of fine lines/wrinkles around the lip.

Figure 2:
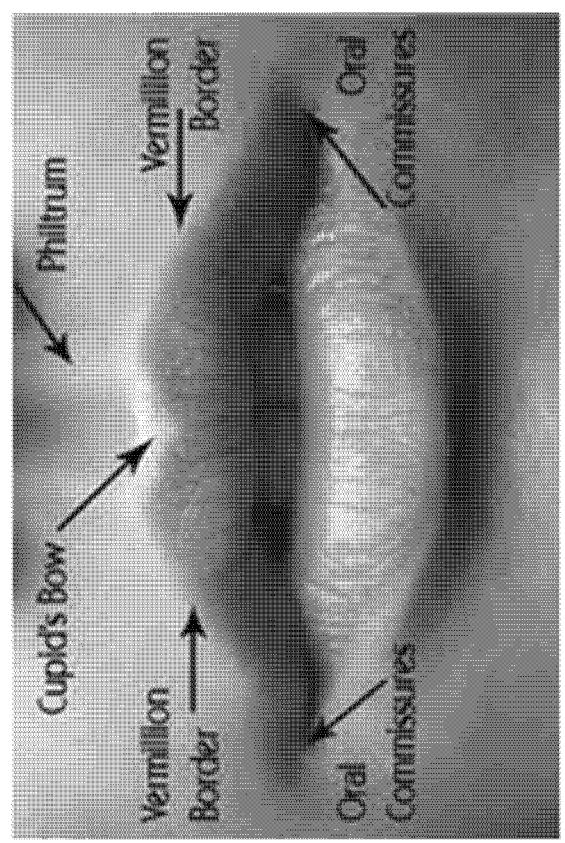
FIG. 2 shows the anatomy of a user's lip region.

FIG. 2 shows the perioral region of a user, and corresponding features, which comprises the lower one third of the face, which consists of the upper and lower lips, the nasolabial folds, and the chin.

Lip tissue is composed of layers including the epidermis, subcutaneous tissue, orbicularis oris muscle fibers, and mucosa, from superficial to deep respectively. Within a top lip and a bottom lip respectively, a superior labial artery and an inferior labial artery course between the orbicularis muscle fibers and the mucosa. The lip tissue includes the vermilion that is composed of non-keratinized squamous epithelium that covers numerous capillaries. The capillaries give the vermilion its characteristic color. Lip tissue further includes numerous minor salivary glands. In an aspect, the lip device can be configured to trigger fiberblast cells within the lip tissue to express proteins, self-proliferate, and generate collagen production.

In an aspect, the lip device can be configured to provide a combined mode of catalytic heating, electromyostimulation, and microsuction to increase the volume of the lip over a longer period of time than any one mode individually. In an example, the combined mode can enhance stimulation of blood flow within the lip allowing the lip volume to increase.

In an example, the microsuction can deliver immediate plumping, the catalytic heating can enhance delivery of necessary actives to the lip tissue, and the electromyostimulation can to stimulate fibroblast cells within the lip tissue to express proteins, proliferate, generate collagen production, as well as firm muscles within and surrounding the lip tissue.

In some implementations, the lip device can further include one or more sensors configured to detect a condition of the lip tissue and/or an operation of the lip device providing a tissue therapy. In an example, one of the one or more sensors can be a pressure sensor configured to detect an absolute and/or change in an amount of suction pressure. In an example, the one or more sensors can be a configured for sensing a lip tissue condition of a portion of lip tissue. In another example, one of the one or more sensors can be a physiologic sensor configured to detect at least one of a change in blood flow and a tissue property.

Referring now to the drawings, wherein like reference numerals designate identical or corresponding parts throughout the several views.

FIG. 1A-1C

Figure 1:
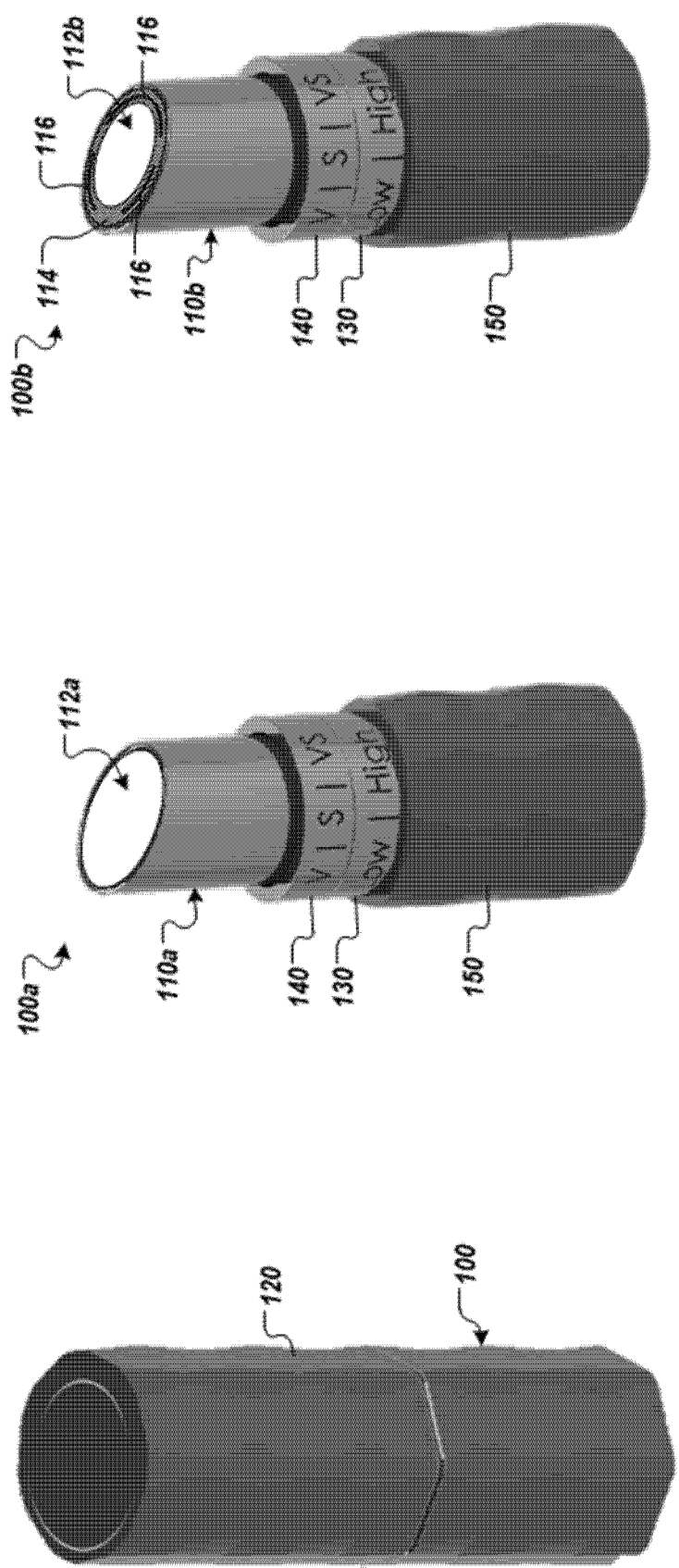
FIG. 1A is a picture of a lip device covered by an end cap according to an example.
FIG. 1B is a picture of a lip device including a mouthpiece having a chamber configured to press against a portion of tissue or lip of a user, a set of controls, and a base portion according to an example.
FIG. 1C is a picture of a lip device including a mouthpiece having an interfacial ring with a set of electrodes, and a chamber according to an example.

FIG. 1A is a picture of a lip device 100 covered by an end cap 120 according to an example. FIG. 1B is a picture of a lip device 100a uncovered including a mouthpiece 110a having a chamber 112a with a distal shape having a cupping curvature configured to press against portion of tissue or lips of a user, a set of controls 130, 140, and a base portion 150 according to an example. In an example, a first set of controls 130 can be configured to control an amount of heat (e.g., low, high). In an example, a second set of controls 140 can be configured to control a mode of operation (e.g., vibration, suction, vibration and suction).

In an example, the mouthpiece 110a can include a silicone layer configured to interface with the lip tissue and aid in creating a seal for the microsuction. In an aspect, the negative pressure is configured to allow the blood vessels within the lip tissue to fill with blood and to trigger an inflammatory response of chemicals such as histamines and leukotrienes. Filling the lip tissue with blood performs a dual function of increasing the lip volume and creating a more rosy lip color.

In an aspect, the lip device is configured to create a cyclic negative pressure to enhance the tissue therapy. In an example, the cyclic negative pressure is configured to generate a vibration at a therapeutic frequency. In an example, the cyclic negative pressure is a change between two or more negative pressures at a therapeutic frequency, each of the negative pressures being returned to atmospheric pressure before the change.

In an aspect, the therapeutic frequency is configured to prevent bruising of the lip tissue and to enhance the tissue therapy. In an example, the therapeutic frequency can be based on the mechanobiology properties of the lip tissue. Different frequencies target different layers of the tissue, such as targeting the mechanical receptors in the cell membranes of fibroblasts and keratinocytes within the lip tissue. This creates a signal cascade within the cells that cause them to create new extracellular matrix proteins. Examples of different frequency ranges in cosmetic devices which have beneficial effects on a user's skin are for example, a "low-frequency" range of about 30 hertz to about 50 hertz which primarily affects epidermis-associated proteins without substantially upregulating dermal-epidermal junction-associated proteins, and dermis-associated proteins; a "mid-frequency" range of about 50 hertz to about 100 hertz which affects all three layers of cutaneous proteins: epidermis-associated proteins, dermal-epidermal junction-associated proteins, and dermis-associated proteins; and a "high-frequency" range of about 100 hertz to about 140 hertz which affects epidermis-associated proteins and dermal-epidermal-junction-associated proteins, but does not substantially affect dermis-associated proteins. The use of frequency ranges is described in each of U.S. PG. Pub. Nos. US2016/0184177A1, US2016/0184176A1, US2016/0184175A1, and US2016/0184171A1, which are incorporated herein by reference.

In an example, the lip device includes a regulator configured to oscillate the vacuum between a negative pressure value and atmospheric pressure at a therapeutic frequency. For instance, the regulator may change the vacuum from a negative pressure value to atmospheric pressure and then back to the negative pressure value over one period. Alternatively, the regulator may change the vacuum between two more negative pressure values at a predetermined frequency. This provides the advantage that when the user performs suctioning, the regulator is configured to modify the negative pressure at the therapeutic frequency.

In an aspect, the catalytic heating is configured to enhance seeping of the actives within the layers of skin on the lip. Further, catalytic heating can be configured to induce an increase in blood flow, leading to increased oxygenation and producing an anti-aging effect. In an example, the catalytic heating can target a specific layer.

FIG. 1C is a picture of a lip device 100b including a mouthpiece 110b having an interfacial ring 114 having a set of electrodes 116 and a chamber 112b according to an example. In an example, the set of electrodes 116 can have different numbers of electrodes (See FIGS. 5B-5C). In an example, the set of electrodes 116 can be configured for sensing a lip tissue condition of a portion of lip tissue. Examples of the lip tissue condition of the portion of lip tissue include an amount of hydration and/or moisture, an amount of cracking, and a thickness.

In an example, the lip device can be configured to perform an electrical impedance spectroscopy on the portion of lip tissue. In an example, the lip tissue condition can be based on a complex impedance sensed using electrical impedance spectroscopy between two or more electrodes on the mouthpiece.

In an example, the lip device can be configured to determine a tissue therapy regimen based on the lip tissue condition.

In an aspect, the set of electrodes 116 can be configured to provide electromyostimulation. In an example, the electromyostimulation is configured to stimulate fiberblast cells within the lip tissue to express proteins, self-proliferate, and generate collagen production. In an aspect, the electromyostimulation is configured to firm the muscles within the lip tissue, which can aid in the skin's ability to reduce aging. In an aspect, the electromyostimulation is configured to cause the lip tissue to increase retention of moisture. In an example, the electromyostimulation can be based on the lip tissue condition. In an example, the electromyostimulation is configured to provide a lip massaging sensation to the user.

FIG. 3A-3C

In an example, the lip device can include one or more accessories such as an applicator and an exfoliator. In an example, the lip device can have a built-in accessory. In an example, the lip device can have replaceable or exchangeable accessories.

Figure 3C:
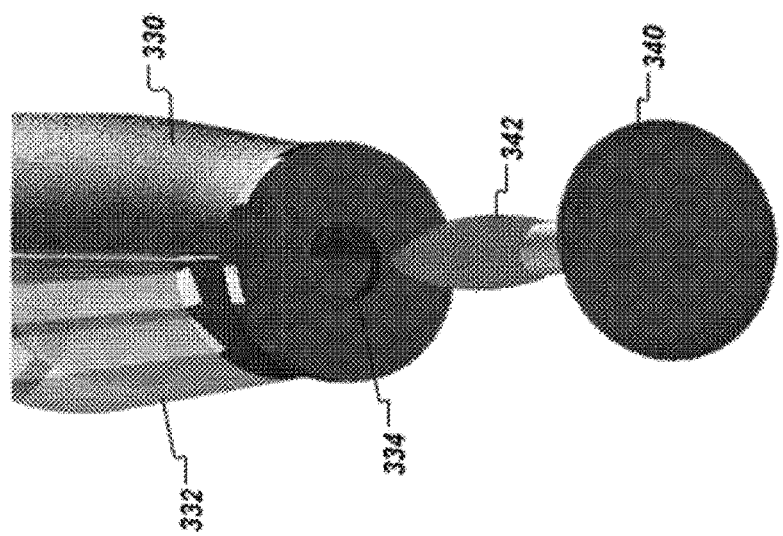
FIG. 3C is a picture of a bottom perspective and expanded view of a portion of the second end cap showing an opening to the topical reservoir configured to receive the applicator plug shown in FIG. 3B according to an example.
Figure 3B:
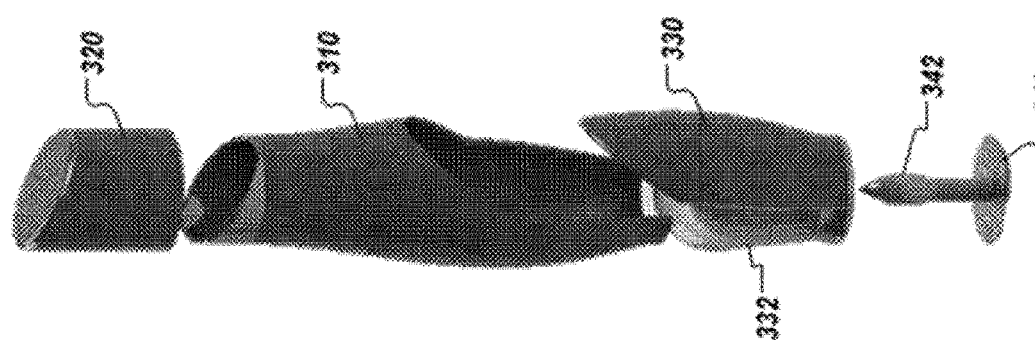
FIG. 3B is a picture of an expanded view of the lip device shown in FIG. 3A according to an example.
Figure 3A:
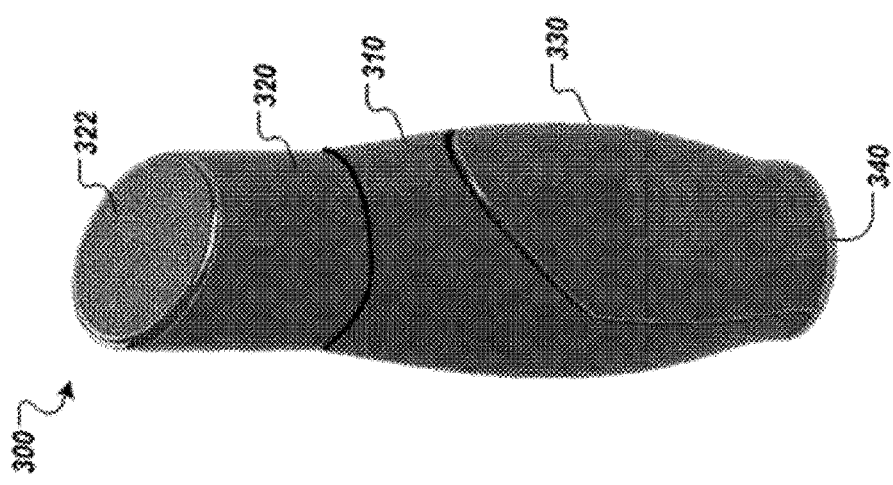
FIG. 3A is a picture of a lip device including a mouthpiece covered with a first end cap, and a second end cap, removably connected to the base portion, having a topical reservoir and an applicator plug according to an example.

FIG. 3A is a picture of a lip device 300 including a mouthpiece 310 covered with a first end cap 320 according to an example. The lip device 300 can further include a second end cap 330 having a topical reservoir 332 and an applicator plug 340 according to an example. FIG. 3B is a picture of an expanded view of the lip device 300 showing the topical reservoir 332 and the applicator plug 340 having a topical applicator 342. FIG. 3C is a picture of a bottom perspective and expanded view of a portion of the second end cap 330 showing an opening 334 to the topical reservoir 332 configured to receive the applicator plug 340 shown in FIG. 3B according to an example.

In an example, the lip device can include an applicator configured to deliver a lip serum to the user's lip. In an example, the lip serum can contain a variety of actives for modifying a lip tissue, supporting the lip tissue, and for modifying a color of the lip tissue.

Examples of actives for modifying the lip tissue include hyaluronic acid microspheres configured to retain moisture in the lip tissue. Examples of actives for supporting the lip tissue include collagen configured to fill in lip lines. Examples of actives for modifying a color of the lip tissue include cinnamon, capsaicin, and wintergreen to restore a natural rosy look to the lips.

FIG. 4A-4C

The lip device can include a suctioner configured to create a negative pressure by removing air within the chamber in several ways.

In some implementations, the lip device can have a vacuum configured to create a negative pressure by removing air from the chamber such that a suction is formed with the lip tissue. FIG. 4A is a drawing of a cross section of a lip device 400a including a mouthpiece 410a having a chamber 420a and a base portion 430a having a vacuum 440 connected to the chamber 420a through a port 424 according to an example. The mouthpiece 410a further includes a heating element 422 and a set of electrodes 470.

The base portion 430a further includes a controller 450 connected to the vacuum 440, a power source 452, and a vibrator 460. In an example, the base portion 430a includes a set of controls 456 in communication with the controller 450. In an example, the controller 450 is connected to other components using electrical connections and circuitry 454. In an example, the vacuum 440 can be configured to oscillate an amount of suction on a portion of lip tissue.

In some implementations, the lip device can have a plunger configured to create a negative pressure by removing air within the chamber. FIG. 4B is a drawing of a cross section of a lip device 400b including a mouthpiece 410b having a chamber 420b and a base portion 430b having a piston 444 configured to move within the chamber 420b while maintaining a seal with an inner surface of the chamber 420b according to an example. The piston 444 can be moved by a motor assembly 442. In an example, the motor assembly 442 can include a set of gears and a set of teeth along a rod connected to the piston 444. In another example, the motor assembly 442 can include a solenoid configured to use a magnetic field to move the rod connected to the piston 444.

The mouthpiece 410b further includes a heating element 422 and a set of electrodes 470. The base portion 430b further includes a controller 450 connected to the motor assembly 442, a power source 452, and a vibrator 460. In an example, the base portion 430a includes a set of controls 456 in communication with the controller 450. In an example, the controller 450 is connected to other components using electrical connections and circuitry 454. In an example, the motor assembly 442 and the piston 444 can be configured to oscillate an amount of suction on a portion of lip tissue. As shown in FIG. 4B, the piston 444 can move from a first position 444' to a second position 444".

In some implementations, the lip device can have a mouthpiece having a flexible diaphragm configured to create a negative pressure by removing air within the chamber. FIG. 4C is a drawing of a cross section of a lip device 400c including a mouthpiece 410c having a flexible diaphragm 428 forming a portion of a chamber 420c, and a base portion 430c having a plunger 448 connected to a motor assembly 446 configured to move the flexible diaphragm 428 within the chamber 420c according to an example. As shown in FIG. 4C, the plunger 448 can move the flexible diaphragm 428 from a first position 428' to a second position 428".

In an example, the heating element 422 can be made from a silicone rubber that can be molded to a shape of the mouthpiece 410a-c. The heating element 422 is preferably moisture resistant and can be controlled by a thermostat such that different settings can be chosen. In some implementations, the heating element 422 can be configured to heat air within the chamber 420a-c such that a suction is formed with the portion of lip tissue when the air within the chamber 420a-c cools.

FIG. 5A-5C

Figure 5A:
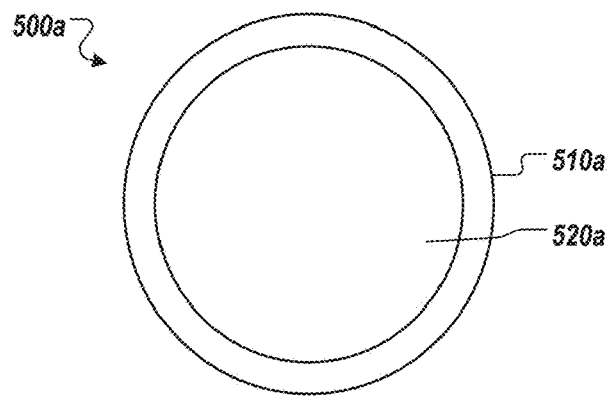
FIG. 5A is a drawing of a distal end of a mouthpiece including an interfacial ring and an opening to the chamber according to an example.
Figure 5B:
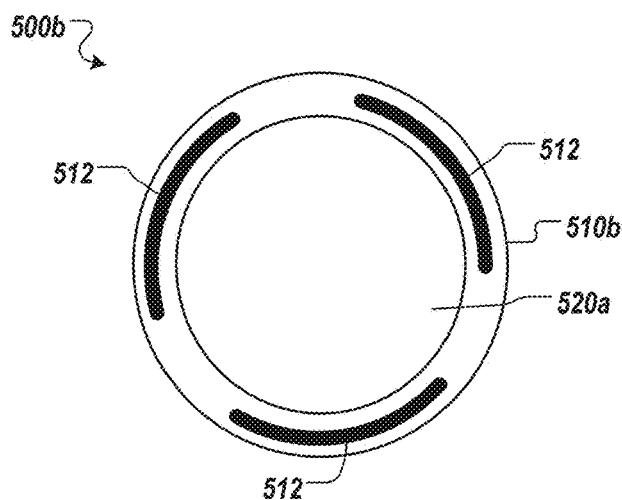
FIG. 5B is a drawing of a distal end of a mouthpiece including an interfacial ring having a set of electrodes according to an example.
Figure 5C:
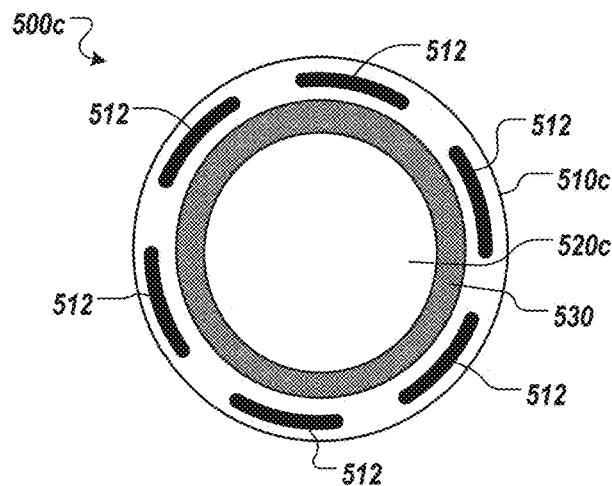
FIG. 5C is a drawing of a distal end of a mouthpiece including an interfacial ring having a set of electrodes and a constrictor according to an example.

FIG. 5A is a drawing of a distal end of a mouthpiece 500a including an interfacial ring 510a and an opening 520a to the chamber according to an example. FIG. 5B is a drawing of a distal end of a mouthpiece 500b including an interfacial ring 510b having a set of electrodes 512 according to an example. FIG. 5C is a drawing of a distal end of a mouthpiece 500c including an interfacial ring 510c having a set of electrodes 512 and a constrictor 530 configured to constrict an opening 520c to the chamber according to an example. In an example, the constrictor 530 can be a removable insert that can be configured for each user. In an aspect, constriction and/or dilation of the constrictor 530 is configured to vary an amount of tissue that is subject to the tissue therapy. In an aspect, constriction and/or dilation of the constrictor 530 is configured to vary an amount of suction pressure applied to the portion of lip tissue. In an example, the constrictor 530 can be electronically controlled by the set of controls and the controller 450. In an example, the constrictor 530 can be manually adjusted.

FIGS. 6A-6E

Figure 6A:
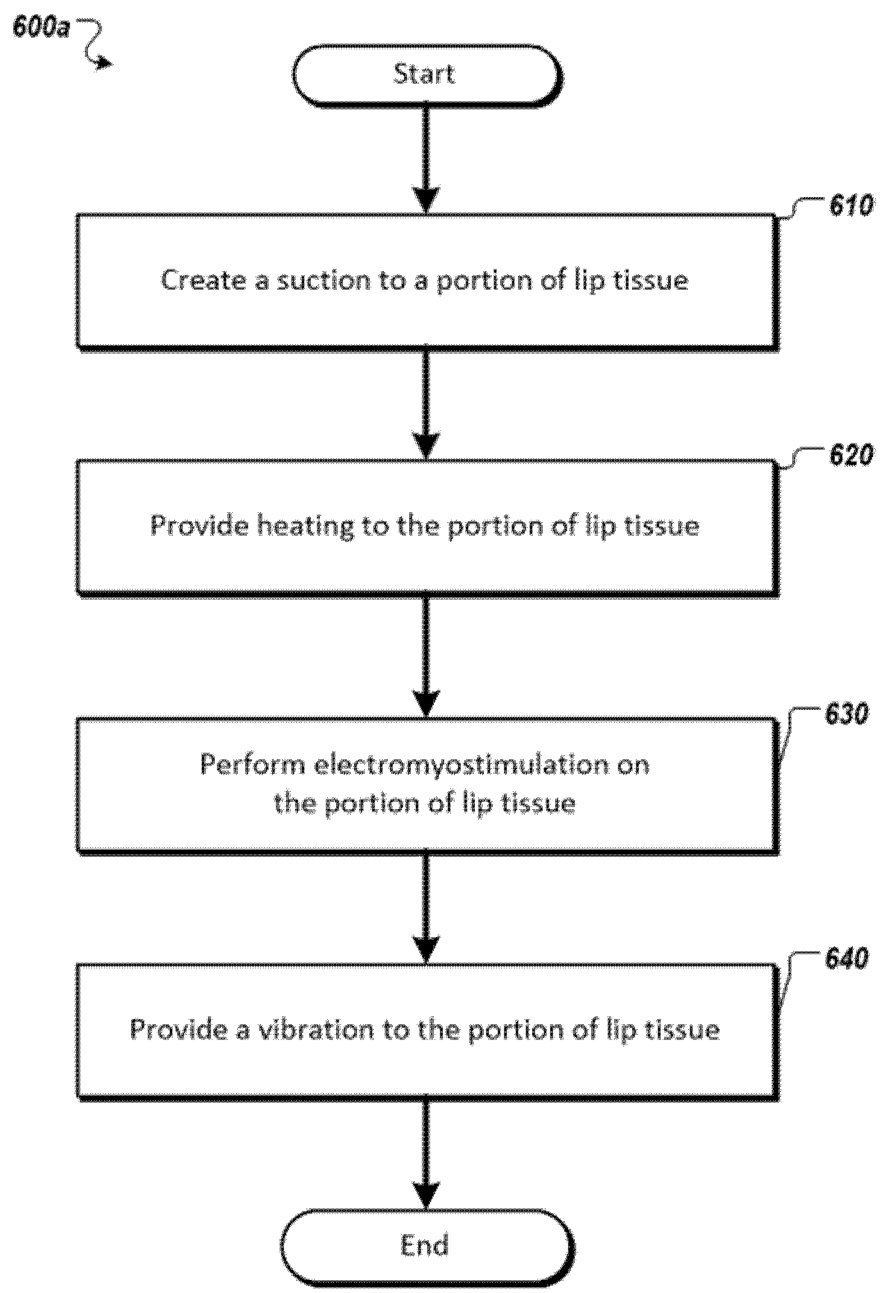
FIGS. 6A, 6B, 6C, 6D, and 6E are flow diagrams describing a method to provide enhanced tissue therapy to a portion of lip tissue of a user according to an example.

FIGS. 6A-6E are flow diagrams describing methods performed at least in part by the controller 450 to provide enhanced tissue therapy to a portion of lip tissue of a user. FIG. 6A is a flow diagram describing a method 600a to provide enhanced tissue therapy to a portion of lip tissue of a user according to an example. The method 600a includes steps of controlling the lip device to create a suction to a portion of lip tissue (610), controlling the lip device to provide catalytic heating to the portion of lip tissue (620), controlling the lip device to provide electromyostimulation of the portion of lip tissue (630), and controlling the lip device to provide a vibration to the portion of lip tissue (640).

Figure 6B:
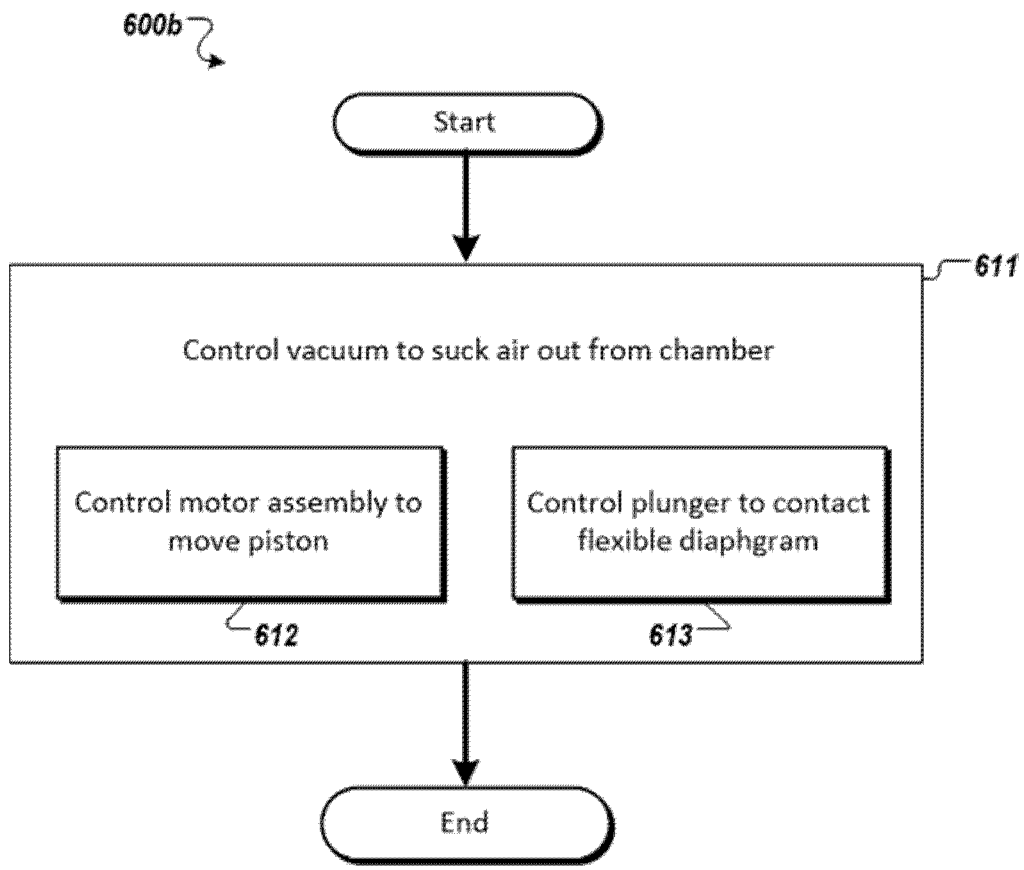

FIG. 6B shows a sub-flow chart on a sub-algorithm 600b for performing step 610, FIG. 6A for creating a suction to a portion of lip tissue. The method includes controlling the vacuum 440 to suck out air from the chamber (611) by controlling the motor assembly 442 to move the piston 444 (612), and controlling the motor assembly 446 to move the plunger 448 in contact with the flexible diaphragm 428 (613).

Figure 6C:
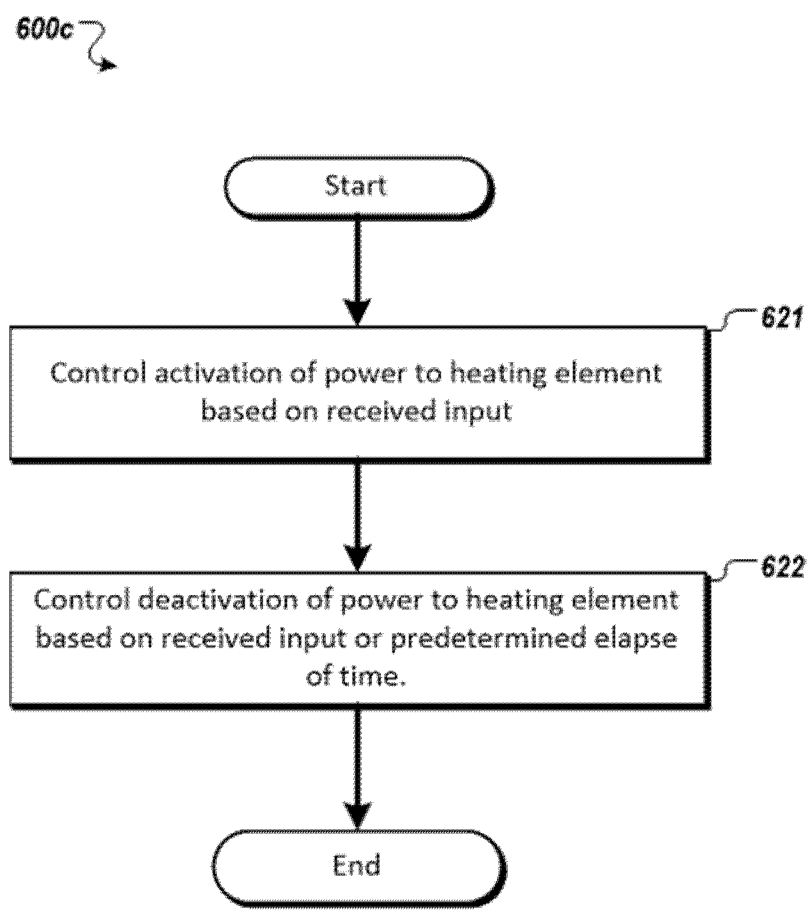

FIG. 6C shows a sub-flow chart on a sub-algorithm 600c for performing step 620 in FIG. 6A for providing heating to a portion of lip tissue. The method includes controlling activation of power to the heating element 422 based on a received input (621) and then deactivating power to the heating element based on a received input or a predetermined elapse of a timer which may be configured to turn off the heat after a predetermined time (622).

Figure 6D:
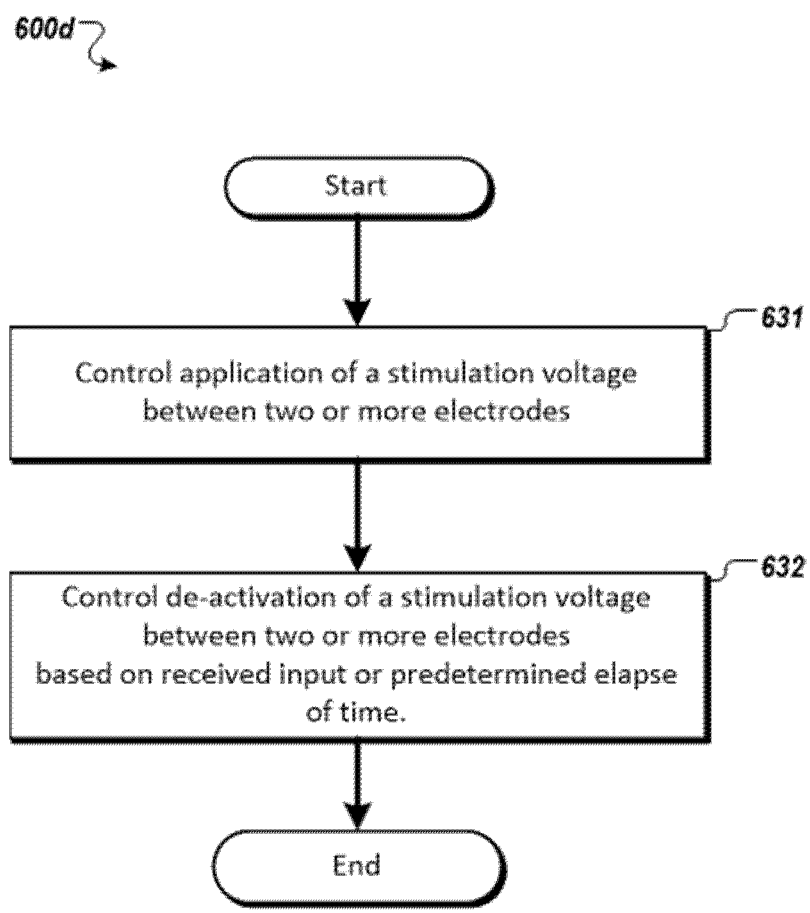

FIG. 6D shows a sub-flow chart on a sub-algorithm 600d for performing step 630 in FIG. 6A for controlling the lip device to provide electromyostimulation of the portion of lip tissue. The method includes applying a stimulation voltage or current between two or more electrodes 116, 470 based on a received input (631) and then de-activating of the stimulation voltage between the two or more electrodes based on received input or predetermined elapse of time (632).

Figure 6E:
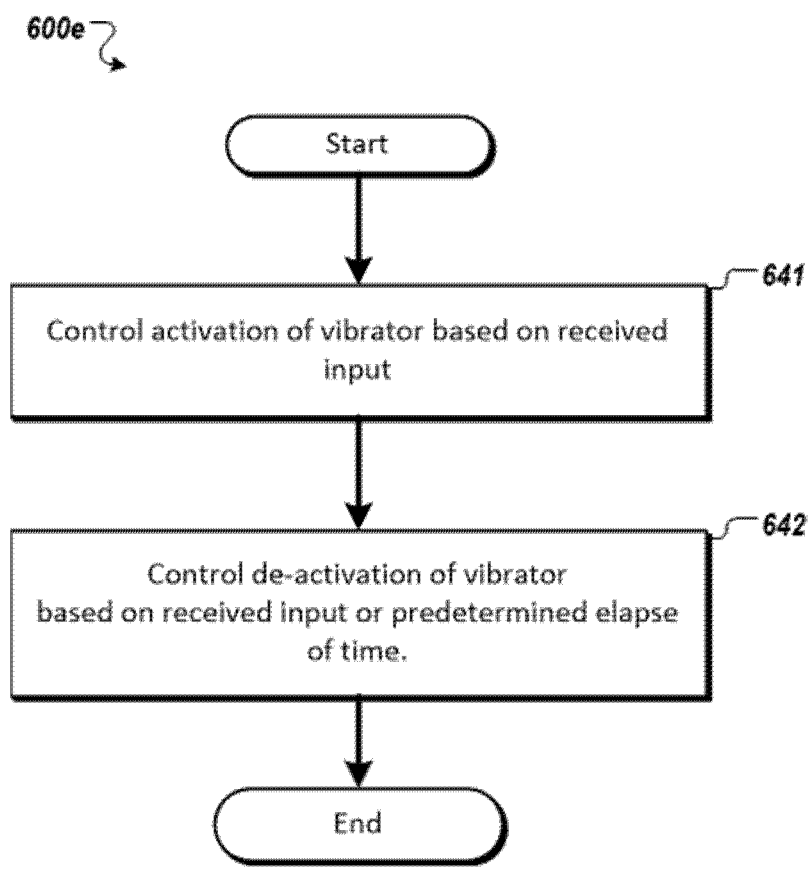

FIG. 6E shows a sub-flow chart on a sub-algorithm 600e for performing step 640 in FIG. 6A for providing a vibration to the portion of lip tissue. The method includes activating the vibrator 460 based on a received input (641) and then de-activating the vibrator 460 based on received input or predetermined elapse of time (642).

FIG. 7A-7E

In some implementations, the lip device can be configured to provide enhanced tissue therapy based on a condition of the lip tissue of the user. FIG. 7 is a flow diagram describing a method 700a to provide enhanced tissue therapy to a portion of lip tissue of a user according to an example. The method 700a includes steps of sensing a lip tissue condition of a portion of lip tissue (710), determining a tissue therapy regimen based on the lip tissue condition (720), providing a tissue therapy to the portion of lip tissue based on the tissue therapy regimen (730). Optionally, the method 700a can further include a step of controlling an indicator based on the lip tissue condition and/or the tissue therapy regimen (740).

Figure 7A:
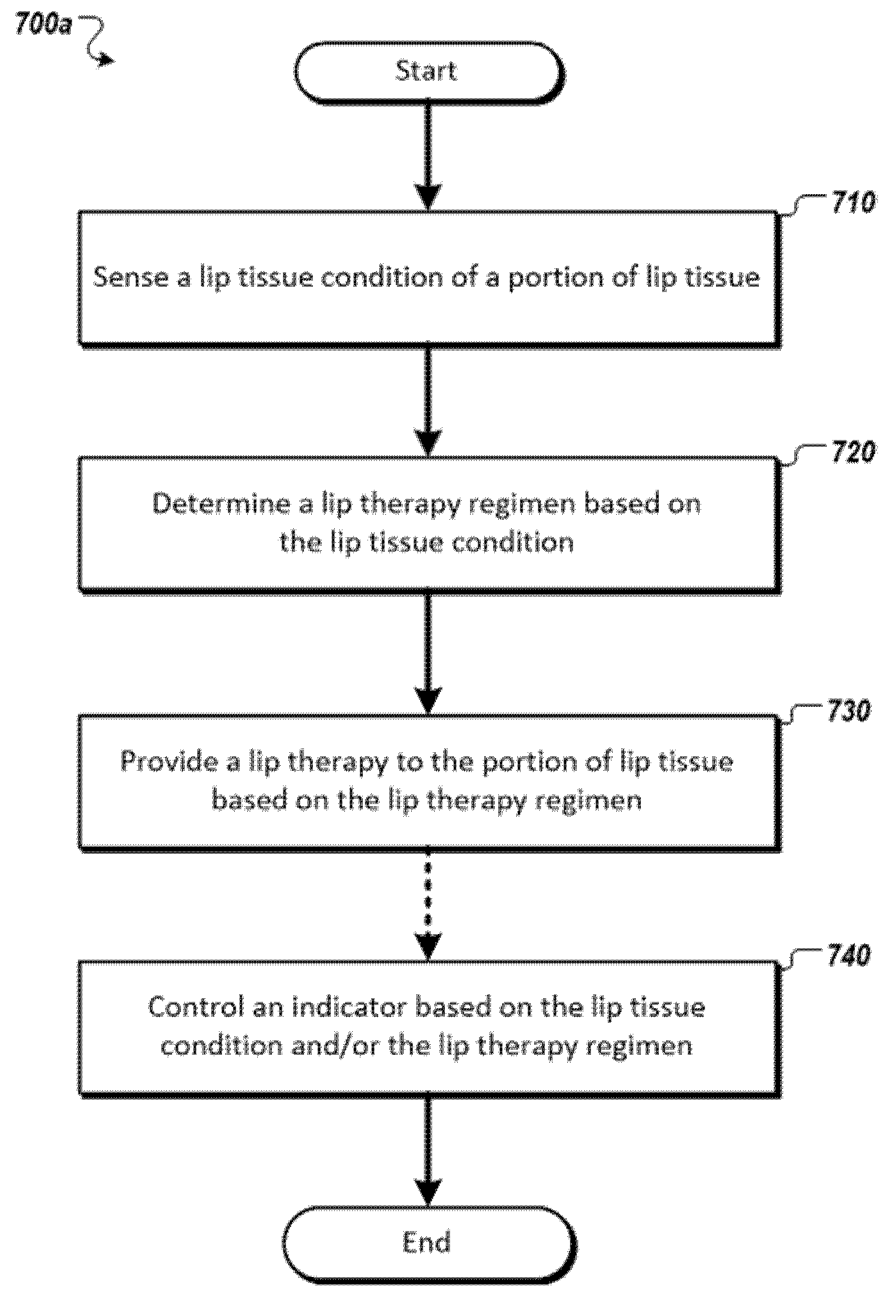
FIGS. 7A, 7B, 7C, 7D, and 7E shows flow diagrams describing a method to provide enhanced tissue therapy to a portion of lip tissue of a user based on a condition of the lip tissue of the user.
Figure 7B:
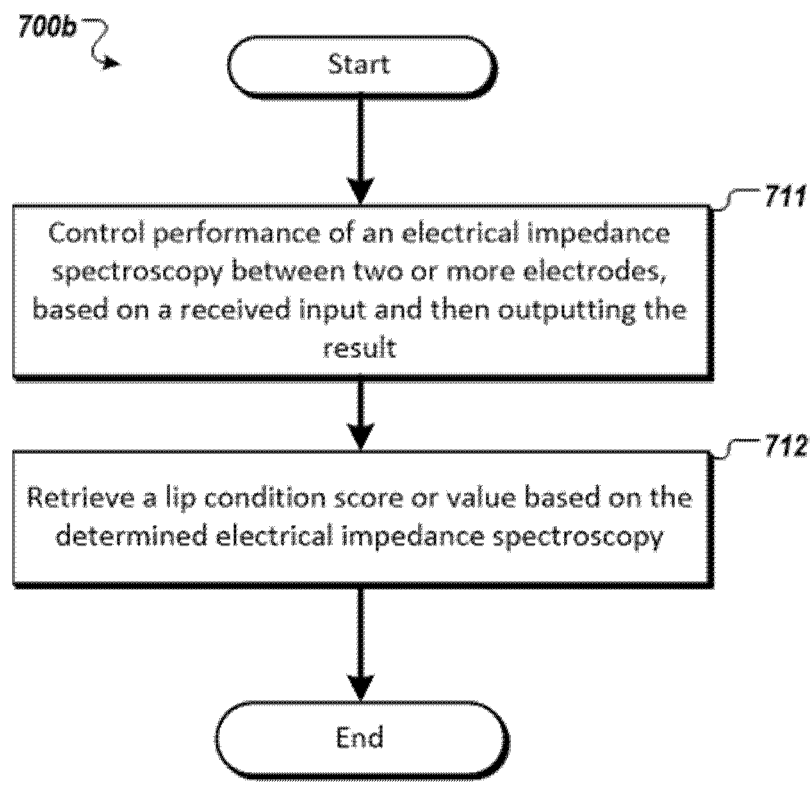

FIG. 7B shows a sub-flow chart on a sub-algorithm 700b for performing step 710 in FIG. 7A for sensing a lip tissue condition of a portion of lip tissue. The method includes controlling performance of an electrical impedance spectroscopy between two or more electrodes 116, 470 based on a received input (711) and then outputting the results. The results may be based on storing a predetermined lip condition scores or values in association with different electrical impedance spectroscopy values or ranges, and retrieving (712) one of the lip condition scores or values based on the determined electrical impedance spectroscopy. All of the predetermined lip condition scores or values in association with different electrical impedance spectroscopy values or ranges, and any look-up tables involved may be stored on an external device, as described in more detail below.

Figure 7C:
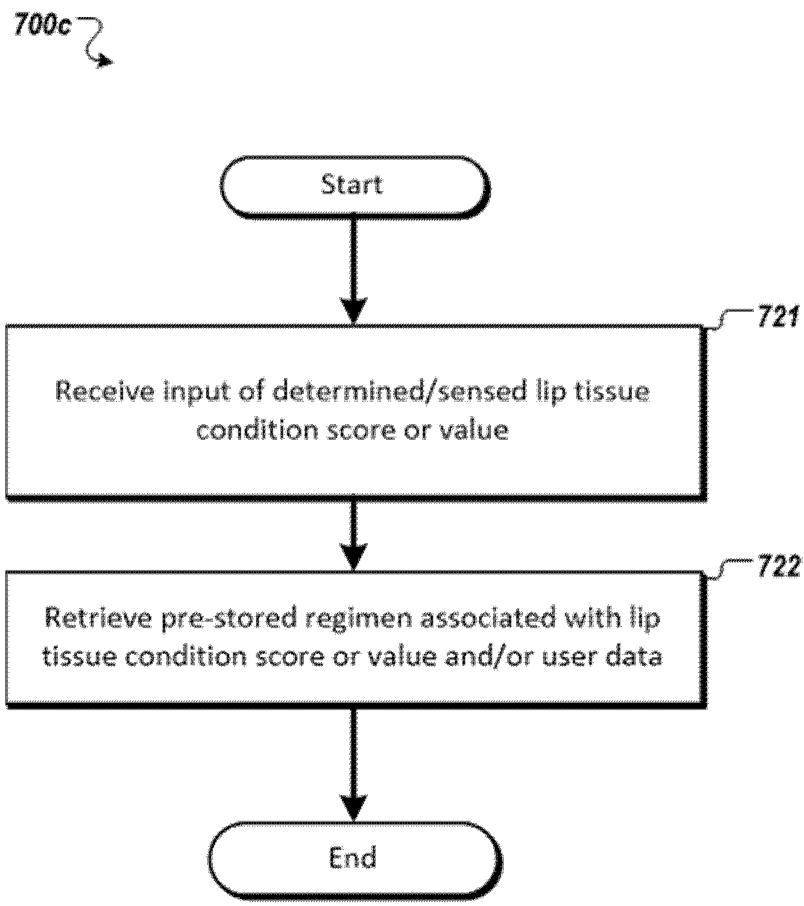

FIG. 7C shows a sub-flow chart on a sub-algorithm 700c for performing step 720 in FIG. 7A for determining a lip therapy regimen based on the sensed lip tissue condition score or value obtained in sub-algorithm 700b which is then provided as an input in the sub-algorithm 700c (721). The method includes retrieving a pre-stored regimen that is associated with the lip tissue condition score or value (722). Alternatively, a pre-stored regimen may be retrieved based on the lip tissue condition score or value in addition to pre-stored user data. The user data may be based on different information on the user stored ahead of time, such as age, natural lip tone, gender, and others. All of the pre-stored data, including any look-up tables which associate the lip tissue condition score/values, pre-stored data, and regimens may be stored on an external device, as described in more detail below.

Figure 7D:
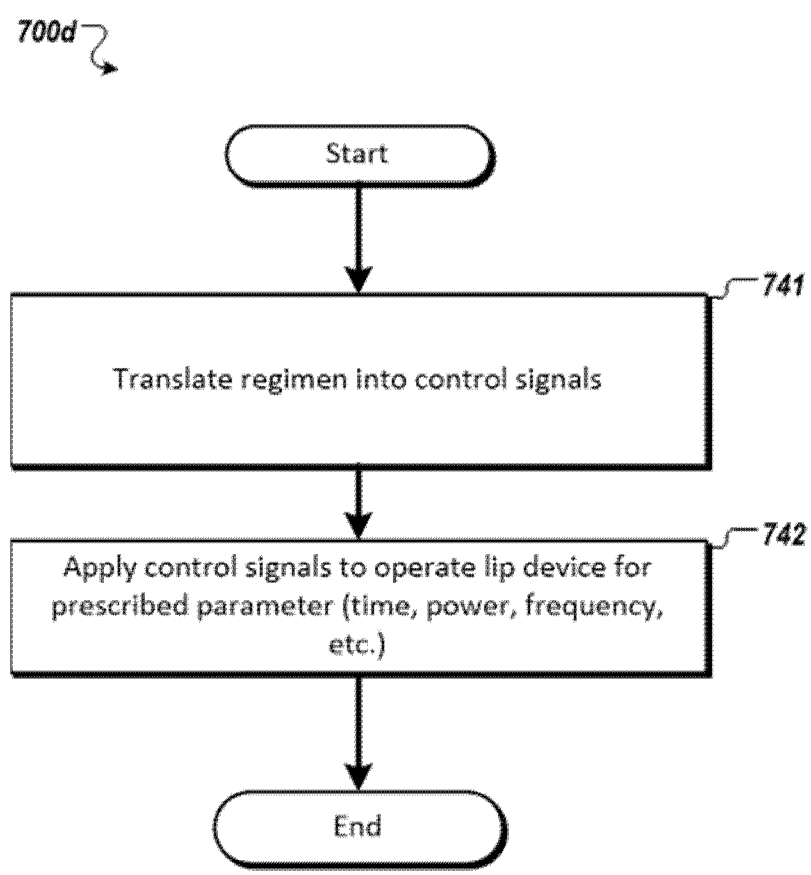

FIG. 7D shows a sub-flow chart on a sub-algorithm 700d for performing step 730 in FIG. 7A for providing a lip therapy to the portion of the lip tissue based on the determined lip therapy regimen. In step 731, the specific therapy regimen is translated into control signals for controlling the lip device. This translation may occur locally within the lip device, or it may occur at an external device with the control signals being transmitted to the lip device. The specific therapy regimen may entail applying a certain type of lip therapy operation provided by the lip device (as described above) for a certain duration, power level, and/or frequency based on the translated control signals (732). Alternately, the therapy regimen may entail a sequence of different types of lip therapy operations in a prescribed order. The therapy regimen may also allow the lip device to be connected to a real-time clock in which the regimen may change based on the time of day.

Figure 7E:
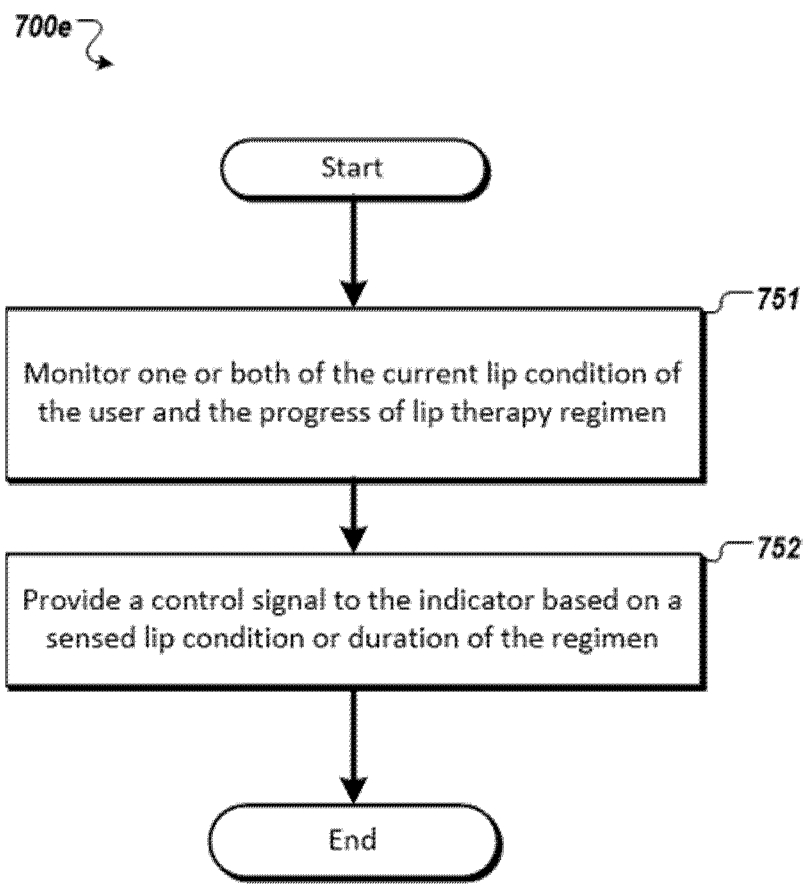

FIG. 7E shows a sub-flow chart on a sub-algorithm 700e for performing step 750 in FIG. 7A for controlling an indicator based on the lip tissue condition and/or the lip therapy regimen. The indicator may be provided on the device itself in the form of a LED indicator light or other visual indicator as known in the art. Alternatively, the indicator may be a display on a connected external device, such as a smartphone or other computer. In step 751, the lip device monitors one or both of the current lip condition of the user and the progress of lip therapy regimen. In step 752, the lip device may provide a control signal to the indicator based on a sensed lip condition or duration of the regimen, such as a green light indicator or a displayed message prompting the user to take a certain action, such as move the device to a different portion of the lips or to end the treatment.

FIG. 8A-8B

Figure 8A:
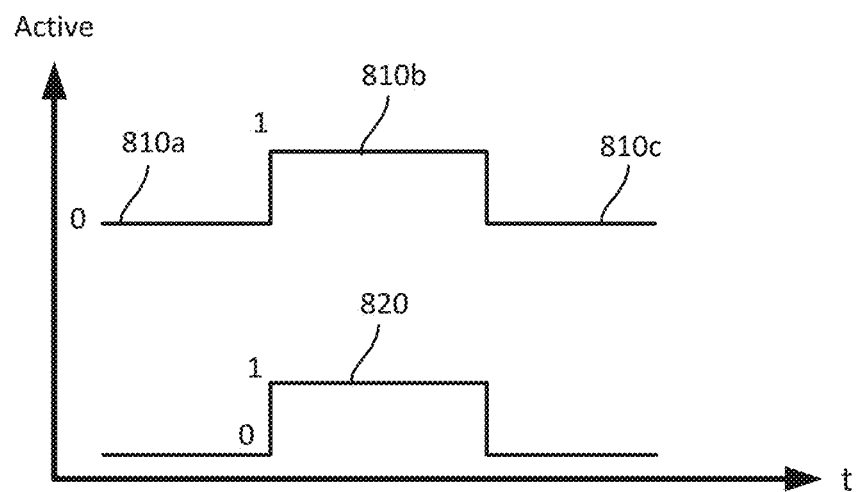
FIG. 8A shows a graph indicating synchronization of a tissue therapy providing a first pulse and a second pulse according to an example.

FIG. 8A shows a graph indicating synchronization of a tissue therapy providing a first pulse 810a-c and a second pulse 820 according to an example. In an example, the first pulse 810a-c can be any tissue therapy modality including suction, electrical stimulation, catalytic heating, and vibration. In an example, the second pulse 820 can include a different tissue therapy modality than the first pulse 810a-c.

Figure 8B:
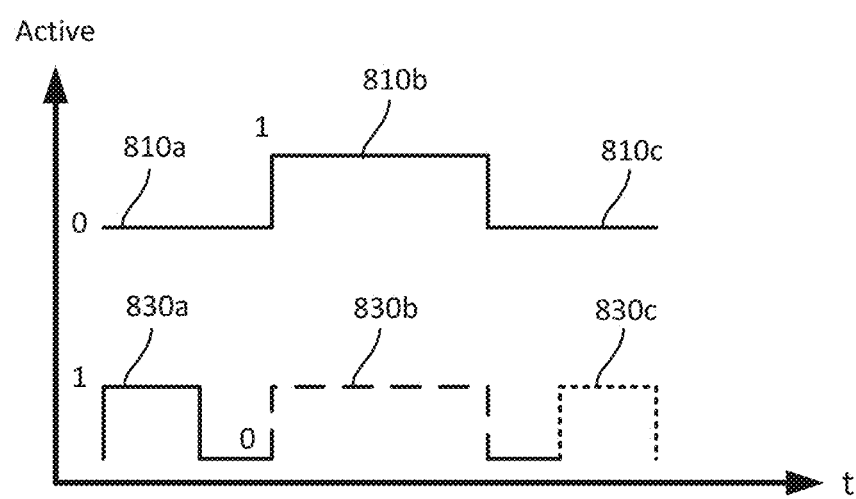
FIG. 8B shows a graph indicating synchronization of a tissue therapy providing an first pulse and a second pulse, where the second pulse includes a pre-pulse and a post-pulse according to an example.

FIG. 8B shows a graph indicating synchronization of a tissue therapy providing an first pulse 810a-c and a second pulse 830a-830c, where the second pulse 830a-830c includes a pre-pulse and a post-pulse according to an example. In an example, the second pulse 830a-830c can include synchronized timing of one or more different tissue therapy modalities. A first tissue therapy modality can be provided prior to activation of the first pulse (810a), a second tissue therapy modality can be provided during activation of the first pulse (810b), and a third tissue therapy modality can be provided after activation of the first pulse (810c). Obviously, numerous modifications and variations of the synchronization of the tissue therapy modalities are possible.

FIG. 9A shows a system 900 that includes lip device 100, as discussed above, and a client device 920. In an embodiment, the lip device 100 is in communication with the client device 920 with a wireless signal 910. In an embodiment, the client device 920 is configured to operate a software application or set of software modules to receive and send communications from and to the lip device 100. In an example, the software application can send a protocol or target profile to the personal cosmetic appliance 100, as well as receive data from the lip device 100 to track the usage in real time.

Figure 9B:
FIGS. 9BA, 9BB, 9BC, 9BD and 9BE show different examples of the client devices according to embodiments.
Figure 9B:
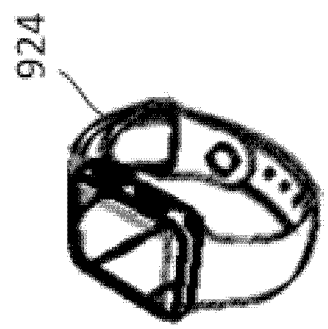
Figure 9B:
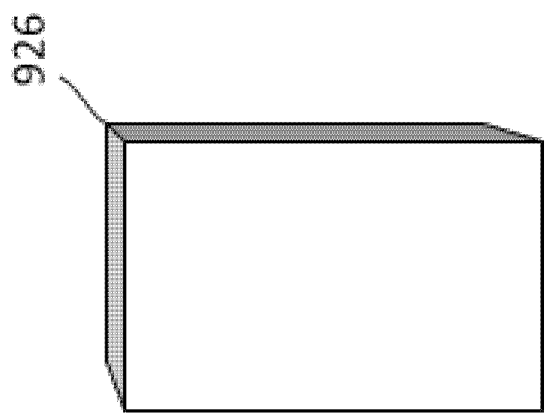
Figure 9B:
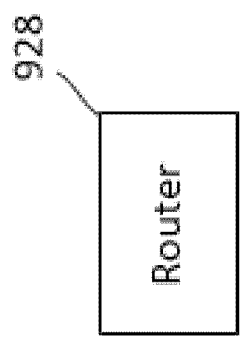
Figure 9B:
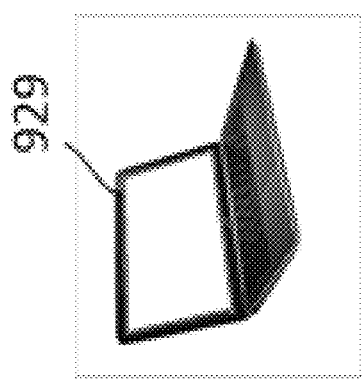

FIGS. 9BA, 9BB, 9BC, 9BD and 9BE show different examples of the client devices 920 including, a mobile device 922, a wearable electronic device 924, a television or magic mirror 926, a network router 928, and a personal computer 929.

The wireless signal 910 can be any appropriate signal such as an electromagnetic signal including WiFi, Bluetooth, near-field, or any other signal such as optical, and acoustic. Each client device, including the appliance, may communicate with each other through an internet connection via an 802.11 wireless connection to a wireless internet access point, or a physical connection to the internet access point, such as through an Ethernet interface. Each connected device is capable of performing wireless communication with other devices, such as through a Bluetooth connection or other wireless means as well.

Figure 9C:
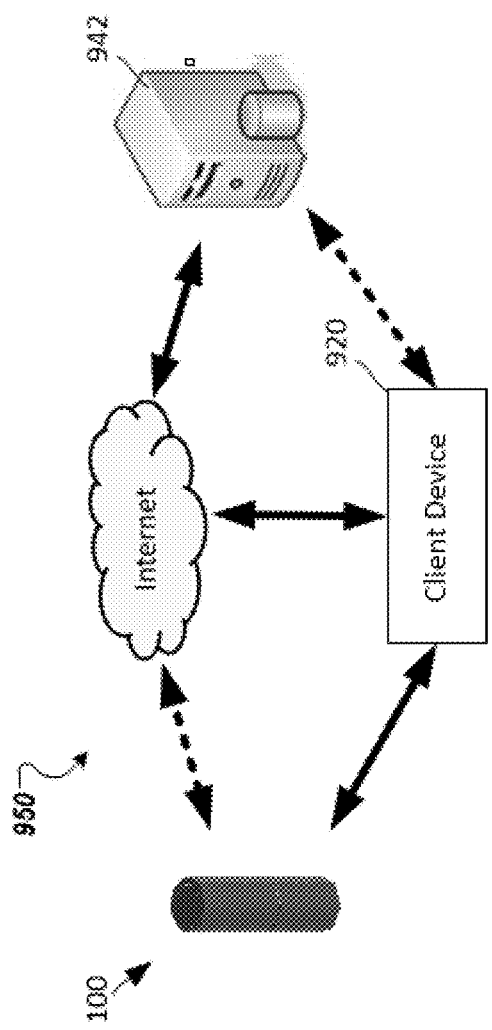
FIG. 9C shows an example of a system to promote optimum performance of a lip device, according to an embodiment.

FIG. 9C is a diagram representing an example of a system 950 used with lip device 100, according to one example. The system 950 includes at least the lip device 100 and the client device 920. Optionally, the system 950 may further include one or more external servers 942 which are implemented as part of a cloud-computing environment and in communication with the system 950 through the Internet. The one or more external servers 942 can store user data, the pre-stored data discussed above with reference to FIGS. 7A-7E, products such as formulations, protocols and regimens, tutorials, as well as other 3rd party services according to an example.

The client device 920 is configured, in one example, to collect information about a user's use of the lip device and to provide output to the user. The operating system of the client device can have a user interface that is configured to perform multiple functions. In an aspect, the client device can be in communication with a network and enable the user interface access to the Internet as well as Internet of Things (IOT). As can be appreciated, the network can be a public network, such as the Internet, or a private network such as an LAN or WAN network, or any combination thereof and can also include PSTN or ISDN sub-networks. The network can also be wired, such as an Ethernet network, or can be wireless such as a cellular network including EDGE, 3G and 4G wireless cellular systems. The wireless network can also be WiFi, Bluetooth, or any other wireless form of communication that is known. In an example, the network can access a server hosting media, protocols, products, personal accounts, stored usage data, and other data related to the appliance, the brushheads, and skin care.

The user interface can display tutorials on how to use the lip device. The client device can create and download protocols for a regimen or routine that can be displayed on the user interface. The user interface can coach, track usage and compare the tracked usage to the protocol, the regimen, and the routine. The user interface can calculate a score based on the tracked usage. The user interface can store the scores and the tracked usage of the personal cosmetic appliance in memory of the client device. The user interface can be used to make a purchase of any products related to the personal cosmetic appliance. For instance, the personal cosmetic appliance may be used with a combination of styling products or chemical compositions used for treating the user's skin or hair, and the client device can output recommendations on particular products to be used, and which step in the process they are to be used, based on the desired results inputted by the user.

As an initial step, the client device may optionally collect information regarding a user's characteristics (such as skin or lip tone, moisture level, or pigmentation analyzed by a sensor on the detachable unit) and usage patterns. The client device may store search results locally or may connect to an external system or server to access the database or search results.

The user may also access tutorials for using the lip device to achieve a target look. The tutorials may be in text form, still image form, video form, or audio-only form.

In addition to using the tutorials, the user may connect the client device 920 with the personal cosmetic appliance over the wireless connection (such as the Bluetooth or Wi-Fi connection) to receive real-time feedback while using the personal cosmetic appliance, or to record the usage of the personal cosmetic appliance for later reporting or feedback.

For example, while using the lip device, a motion sensor on the lip device can output a detected motion of the personal cosmetic appliance as feedback to the client device. The client device is configured to compare the detected motion with predetermined motion data for providing real-time performance results to the user to or to output instructions for the user to make a correction.

The client device can also have a camera function that can be used to provide inputs to the customer profile. For instance, the camera can take images of the user's lip tone to determine the state of the user's lips based on visual data, or to make further recommendations to the user based on the characteristics of the lips.

The client device is configured to upload data regarding the user to an external system or server (such as a cloud-based system). Such data may include the user profile, amount of use of the personal cosmetic appliance, or performance results when using the personal cosmetic appliance. The client device can also provide an option to keep the user data anonymous.

The client device can use the camera function to provide a sharing feature, in which the user can upload photos taken before and/or after the use of the personal cosmetic appliance. The uploaded photos can be used for receiving feedback from professionals in the skin (or hair) treatment industry or other users. In an embodiment, the uploaded photos may be uploaded directly to a social media platform.

Furthermore, the circuitry of the lip device 100 may be configured to actuate a discovery protocol that allows the main unit or the detachable unit and a remote enterprise to identify each other and to negotiate one or more pre-shared keys, which further allows the main unit or the detachable unit and a remote network to exchanged encrypted and anonymized information. The discovery protocol may further allow the main unit or the detachable unit and a remote network to exchange treatment regimen information depending on the type of applicator included in the detachable unit.

Furthermore, the circuitry of the lip device may be configured to exchange control commands with a remote network, such that a remote device may externally control the lip device.

Advantages

The lip device provides a non-invasive, effective method of achieving fuller lips. Using multiple modalities, the lip device provides enhanced penetration of actives into the lip and surrounding skin. Further, the lip device provides sustained benefits after use including maintaining moisture on the lips to avoid dryness and chapping.

Additionally, there is an "ideal lip ratio" that is well known in the art of dermatology. The lower: upper lip ratio should be 1.6:1. Therefore, the present embodiments, and in particular the use of the above-described screen, allow for consumers to better achieve this ratio by focusing on improving the volume in the lip in select areas that they need. Also, the contour 114 (cupping curvature) of the device can be specially designed to help consumers better achieve the ideal lip volume ratio discussed above.

A benefit of the device according to the above-described embodiments is that it will be smaller, more compact, travel friendly and quieter than other devices in the conventional art. Thus, the present design and functional modifications of the present embodiments are more desirable to the consumer since a device meeting all of these criteria does not exist on the market today.

The present embodiments allow consumers to achieve (i) immediate benefits in lip volume/plumping and natural lip color enhancement and (ii) longer term lip volume/plumping benefits after daily use (vs. initial baseline). The present embodiments further provide an advantage of delivering multiple lip enhancement benefits without the need for injections, needles, potential side effects, surgery or potentially skin sensitizing chemicals that are commonly used to achieve lip enhancement effects.

The foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernable variants of the teachings herein, define, in part, the scope of the foregoing claim terminology such that no inventive subject matter is dedicated to the public.

Obviously, numerous modifications and variations of the present disclosure are possible in light of the above teachings. It is therefore to be understood that within the scope of the appended claims, the invention may be practiced otherwise than as specifically described herein.

The invention claimed is:

1. A lip conditioning device for providing enhanced tissue therapy to lip tissue of a user, the device comprising:
   a mouthpiece having a chamber with a distal end configured to create a seal with a portion of the lip tissue of the user;
   a base portion, connected to the mouthpiece, including a controller in communication with a power source, and a suction device configured to remove air within the chamber;
   a set of controls, in communication with the controller, configured to control a mode of operation of the tissue therapy;
   a heater configured to provide heat to the lip tissue of the user;
   an applicator configured to deliver a lip serum to the lip tissue of the user, wherein the heater is configured to perform catalytic heating to enhance delivery of active ingredients of the lip serum within layers of the lip tissue of the user; and
   a constrictor that is a removable insert and is configured to constrict an opening of the chamber and the opening is configured to be constricted and dilated to vary an amount of suction pressure applied to the portion of the lip tissue.

2. The lip conditioning device of claim 1, wherein the suction device includes a vacuum configured to oscillate at a predetermined frequency, where the vacuum changes from a negative pressure value to atmospheric pressure and then back to the negative pressure value over one period.

3. The lip conditioning device of claim 2, wherein a regulator is configured to oscillate the vacuum between two or more negative pressure values at a predetermined frequency.

4. The lip conditioning device of claim 1, wherein the suction device includes a piston and a motor assembly configured to move the piston, and
wherein the piston is configured to move within the chamber while maintaining a seal with an inner surface of the chamber.

5. The lip conditioning device of claim 1, wherein the mouthpiece has a flexible diaphragm forming a portion of the chamber,
wherein the base portion has a plunger connected to a motor assembly configured to move the flexible diaphragm within the chamber.

6. The lip conditioning device of claim 1, further comprising one or more electrodes configured to sense a lip tissue condition of the portion of the lip tissue of the user.

7. The lip conditioning device of claim 6, wherein the lip tissue condition is at least one of an amount of hydration and/or moisture, an amount of cracking, and a thickness related to the lips of the user.

8. The lip conditioning device of claim 6, wherein the lip conditioning device is configured to provide the tissue therapy to the lip tissue of the user based on a tissue therapy regimen that is determined based on the sensed lip tissue condition of the user.

9. The lip conditioning device of claim 8, wherein the lip conditioning device is configured to communicate the sensed lip tissue condition to an external device, and the external device determines and transmits control information for administering the tissue therapy regimen to the lip conditioning device based on the sensed lip tissue condition.

10. The lip conditioning device of claim 6, wherein the one or more electrodes are disposed surrounding the opening of the chamber.

11. The lip conditioning device of claim 6, wherein the one or more electrodes are configured to provide electromyostimulation to the lip tissue of the user.

12. The lip conditioning device of claim 1, further comprising a vibrating element configured to provide a vibration to the lip tissue of the user at a predetermined frequency.

13. A method, implemented by a lip conditioning device for providing enhanced tissue therapy to lip tissue of a user, comprising:
sensing a lip tissue condition of a portion of the lip tissue;
determining a tissue therapy regimen based on the lip tissue condition;
automatically providing a tissue therapy to the portion of the lip tissue based on the tissue therapy regimen;
providing, via a heater, heat to the lip tissue of the user;
delivering, via an applicator, a lip serum to the lip tissue of the user, wherein the heater is configured to perform catalytic heating to enhance delivery of active ingredients of the lip serum within layers of the lip tissue of the user; and
constricting, via a constrictor that is a removable insert, an opening of the chamber and varying an amount of suction pressure applied to portion of the lip tissue, by constricting or dilating the constrictor.

14. The method according to claim 13, wherein the tissue therapy includes at least one of:
providing electromyostimulation of the portion of lip tissue; and
providing a vibration to the portion of lip tissue.

15. A system comprising:
a lip conditioning device for providing enhanced tissue therapy to lip tissue of a user, the lip conditioning device including
a mouthpiece having a chamber with a distal end configured create a seal with a portion of the lip tissue of the user,
a base portion, connected to the mouthpiece, including a controller in communication with a power source, and a suction device configured to remove air within the chamber, and
a set of controls, in communication with the controller, configured to control a mode of operation of the tissue therapy; and
an information processing device configured to communicate with the lip conditioning device and provide control information for controlling the mode of operation,
the lip conditioning device further comprising:
a heater configured to provide heat to the lip tissue of the user;
an applicator configured to deliver a lip serum to the lip tissue of the user, wherein the heater is configured to perform catalytic heating to enhance delivery of active ingredients of the lip serum within layers of the lip tissue of the user; and
a constrictor that is a removable insert and is configured to constrict an opening of the chamber and the constrictor is configured to be constricted and dilated to vary an amount of suction pressure applied to the portion of the lip tissue.

* * * * *

UNITED STATES PATENT AND TRADEMARK OFFICE
CERTIFICATE OF CORRECTION

PATENT NO. : 10,905,623 B2
APPLICATION NO. : 15/663150
DATED : February 2, 2021
INVENTOR(S) : Kelly George et al.

Page 1 of 2

It is certified that error appears in the above-identified patent and that said Letters Patent is hereby corrected as shown below:

On the Title Page

Column 1, Item (51), under "Int. Cl.", Lines 1-2, delete
"*A61H 9/00*   (2006.01)
*A61H 23/00*   (2006.01)" and insert --*A61H 9/00*   (2006.01)--;

Column 2, Item (56), under "OTHER PUBLICATIONS", Line 1, delete "Repot" and insert --Report--;

On Page 2, Column 1, Item (51), under "Int. Cl.", Lines 1-9, delete
"*A61M 1/00*   (2006.01)
*A61N 1/32*    (2006.01)
*A61B 5/00*    (2006.01)
*A61N 1/18*    (2006.01)
*A61B 5/053*   (2006.01)
*A61N 1/04*    (2006.01)
*A45D 44/22*   (2006.01)
*A61H 7/00*    (2006.01)
*A61M 1/08*    (2006.01)".

In the Claims

In Column 12, Claim 1, Line 67, delete "chamber" and insert --chamber,--;

In Column 13, Claim 6, Line 26, delete "a lip" and insert --the lip--;

In Column 14, Claim 13, Line 14, delete "portion" and insert --the portion--;

In Column 14, Claim 15, Line 25, delete "including" and insert --including:--;

Signed and Sealed this
Third Day of August, 2021

Drew Hirshfeld
*Performing the Functions and Duties of the
Under Secretary of Commerce for Intellectual Property and
Director of the United States Patent and Trademark Office*

In Column 14, Claim 15, Line 27, delete "of the lip" and insert --of lip--; and

In Column 14, Claim 15, Line 50, delete "chamber" and insert --chamber,--.